(12) United States Patent
Bisrat et al.

(10) Patent No.: US 6,346,523 B1
(45) Date of Patent: Feb. 12, 2002

(54) BUDESONIDE PARTICLES AND PHARMACEUTICAL COMPOSITIONS CONTAINING THEM

(75) Inventors: Mikael Bisrat; Saeed Moshashaee, both of Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/091,453

(22) PCT Filed: May 15, 1998

(86) PCT No.: PCT/SE98/00908

§ 371 Date: Jun. 18, 1998

§ 102(e) Date: Jun. 18, 1998

(87) PCT Pub. No.: WO98/52544

PCT Pub. Date: Nov. 26, 1998

(30) Foreign Application Priority Data

May 23, 1997 (SE) .............................. 9701956

(51) Int. Cl.[7] .............................. A61L 9/04; A61K 9/14
(52) U.S. Cl. .................. 514/172; 514/178; 514/179; 514/181; 514/951; 424/489; 424/43; 424/44; 23/297; 23/299; 210/634; 210/702; 210/709; 210/713; 210/773; 210/774; 210/808
(58) Field of Search .................. 514/172, 178, 514/179, 181, 951; 424/489, 43, 44; 23/297, 299; 210/634, 702, 709, 713, 773, 774, 808

(56) References Cited

U.S. PATENT DOCUMENTS

| 5,254,330 | A | | 10/1993 | Ganderton et al. |
| 5,314,506 | A | | 5/1994 | Midler, Jr. et al. ............ 23/295 |
| 5,674,860 | A | * | 10/1997 | Carling et al. ............... 514/171 |
| 5,709,884 | A | | 1/1998 | Trofast et al. |
| 5,874,063 | A | * | 2/1999 | Briggner et al. ............... 424/45 |

FOREIGN PATENT DOCUMENTS

| EP | 0169618 A2 | 1/1986 |
| WO | WO 90/03782 | 4/1990 |
| WO | WO 95/01221 | 1/1995 |
| WO | WO 95/05805 | 3/1995 |
| WO | WO 96/32095 | 10/1996 |

OTHER PUBLICATIONS

PCT Search Report (3 pages).
Debendetti et al., "Application of Supercritical Fluids for the Production of Sustained Delivery Devices", J. of Controlled Release, 24:27–44, 1993.
Phillips et al., "Rapid Expansion From Supercritical Solutions: Application to Pharmaceutical Processes", Int'l. J. of Pharmaceuticals, 94:1–10, 1993.
Streckel et al, "Micronizing of steroids for pulmonary delivery by supercritical carbon dioxide", Internat'l J. of Pharmaceutics, 152:99–110, 1997.

* cited by examiner

Primary Examiner—Frederick Krass
(74) Attorney, Agent, or Firm—Fish & Richardson P.C.

(57) ABSTRACT

The invention provides finely divided, substantially crystalline particles of budesonide characterized in that they are substantially smooth and having a BET value from 1 to 4.5 $m^2/g$, process for their preparation, a pharmaceutical composition comprising said particles, the use of said particles in the treatment of and in the manufacture of a medicament for use in the treatment of a respiratory disorder, and a method of treatment of respiratory disorders by administration of said particles to a host in need of such treatment.

15 Claims, 2 Drawing Sheets

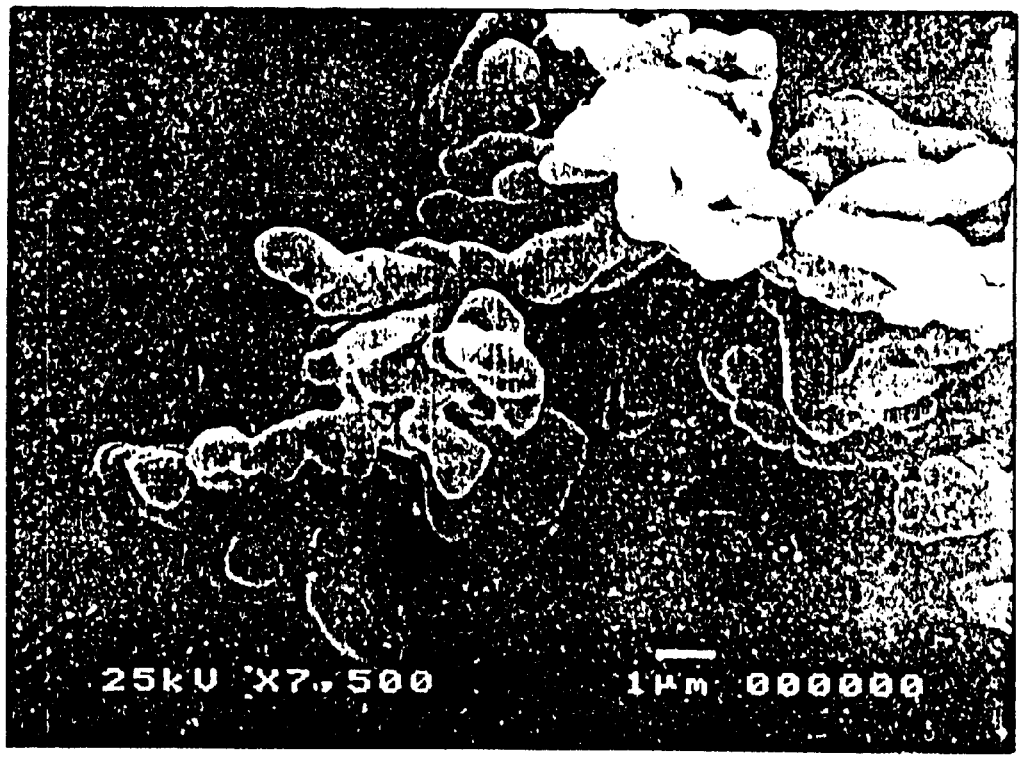

mal Activity monitor. The measurement was carried out by
BUDESONIDE PARTICLES AND PHARMACEUTICAL COMPOSITIONS CONTAINING THEM This is a 371 of International Patent Application No. PCT/SE98/00908, with an international filing date of May 15, 1998, now pending.

BACKGROUND OF THE INVENTION

The invention provides finely divided particles of budesonide and a process for their preparation. The invention also relates to a pharmaceutical composition comprising said particles, the use of said particles in the treatment of and in the manufacture of a medicament for use in the treatment of a respiratory disorder, and a method of treatment of respiratory disorders by administration of said particles to a host in need of such treatment.

Finely divided particles of budesonide are used in therapy in administration by inhalation where it is desired that the drug particles penetrate deep into the lung. Conventionally these finely divided drug particles are made by techniques such as micronization or grinding. A number of other techniques for their production are also available. Such techniques, and in particular micronization, can produce particles which have regions of partially amorphous structure and which have an irregular shape, but which are generally sufficiently stable for pharmaceutical use. However, these particles are liable to change their structure when kept in an adverse environment, such as is usual when a drug is stored (e.g. in high humidity which can cause agglomeration), and/or is in use by a patient. In the past the problem of the amorphous areas has been overcome by subjecting the particles to a conditioning process such as that disclosed in WO 95/05805 but the problem with the irregular shape of the particles remains. The shape of the particles is important because any irregularity increases the tendency of the particles to stick together. Thus they are harder to disperse in the lung. A solution to these problems has been sought.

SUMMARY OF THE INVENTION

According to the present invention the problem has been solved by providing finely divided, substantially crystalline particles of budesonide characterised in that they are substantially smooth and have a surface area BET gas absorption value of from 1 to 4.5 preferably from 2.0 to 4.5, preferably 2.0 to 3.6 m$^2$/g.

The well-defined small particles of the present invention are a prerequisite for an efficient formulation for inhalation, which may be observed by e.g. an increased fraction of the dose to the lung. Crystals with a low surface area have lower tendency to stick together than crystals with a higher surface area e.g irregular crystals.

The surface area was measured by BET gas absorption, e.g. as measured by a Flowsorb II 2300 or Gemini 2370, Micromeritics Co, USA, and described in ISO/TC24SC4N 55 (7th draft) and references therein.

The smoothness of the particles of the invention is illustrated by FIG. 1 which is a Scanning Electron Micrograph (SEM) of the particles of the invention taken using a JEOL Scanning Microscope JSM-5200.

It is preferred that the finely divided particles according to the invention have a mass median diameter (MMD) of less than 10 μm, preferably less than 5 μm, more preferably less than 3 μm.

The particles according to the invention have a substantially crystalline form, preferably at least 95% by weight crystallinity wherein there are substantially no amorphous areas. The crystallinity of the particles of the invention is illustrated by the X-ray diffraction pattern of FIG. 2. Preferably the particles of the invention have an energy of recrystallization of less than 1.0 J/g, more preferably less than 0.5 J/g, as measured using a ThermoMetric 227 Thermal Activity monitor. The measurement was carried out by exposing samples of the particles to a temperature of 25° C. and 94% relative humidity for 24 hours and recording the amount of heat given off by the sample.

BRIEF DESCRIPTION OF THE DRAWINGS

FIG. 1 is a Scanning Electron Micrograph of the particles according to one embodiment of the invention.

DETAILED DESCRIPTION OF PREFERRED EMBODIMENTS

Figure 2:
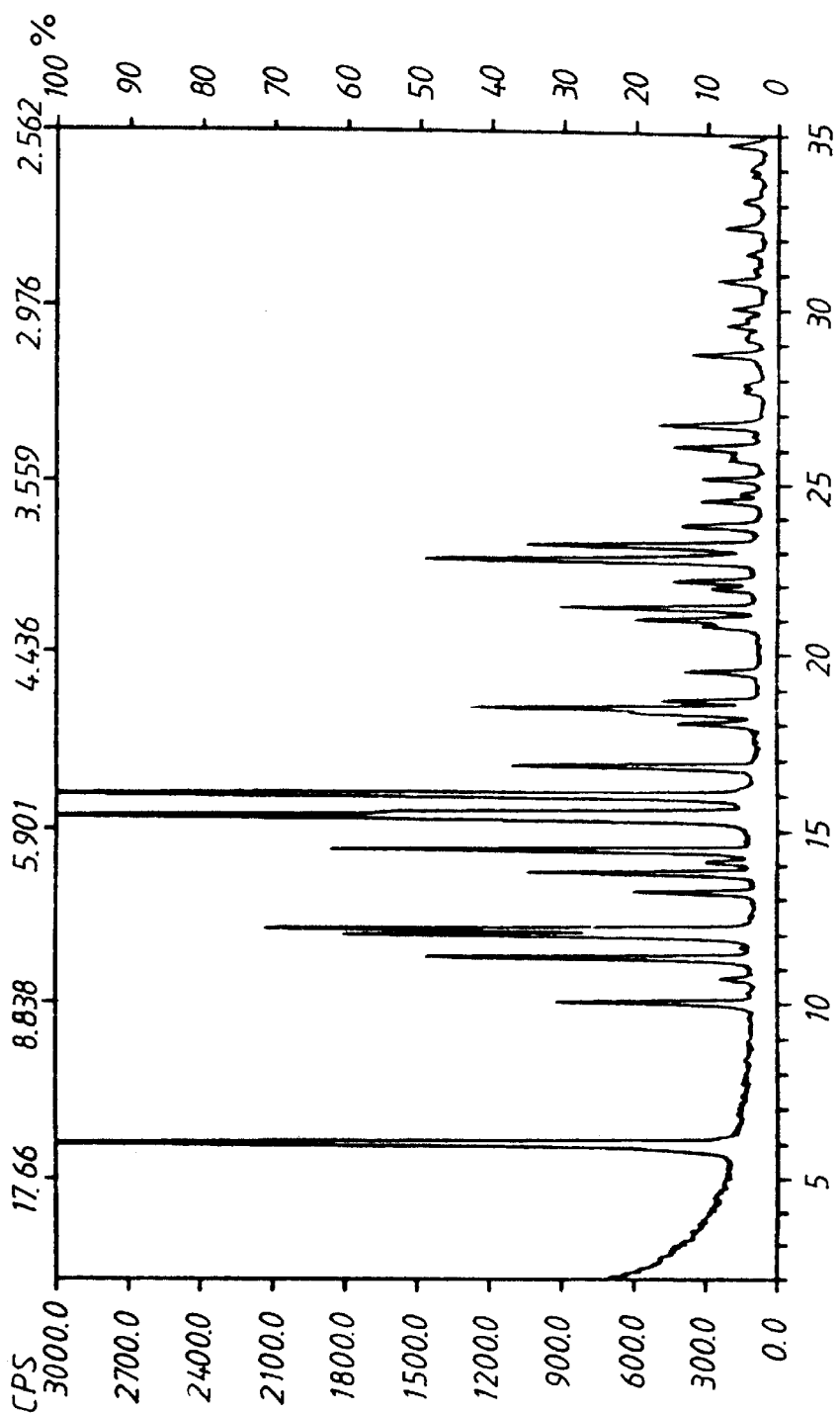
FIG. 2 is an X-ray powder diffraction pattern of particles formed according to Example 2, below.

The finely divided particles of the invention may be prepared by the co-introduction of (a) a solution of budesonide in a solvent and of (b) a supercritical fluid into an apparatus, wherein the temperature and pressure of the apparatus are controlled such that dispersion and extraction of the solvent by the action of the supercritical fluid occur substantially simultaneously. Thus the active substance, budesonide, precipitates directly into small respirable particles having the desired physio-chemical properties. A supercritical fluid is, in general, a fluid at or above both its critical pressure and critical temperature; it is preferably carbon dioxide. The solvent used to dissolve budesonide is preferably an organic solvent, e.g. acetone or methanol. Preferably the process is carried out using the apparatus disclosed in WO 95/01221.

The finely divided particles according to the invention are preferably for use in the treatment of a respiratory disorder, e.g. asthma. The invention further provides a pharmaceutical composition comprising finely divided particles according to the invention in association with a pharmaceutically acceptable carrier or diluent, e.g. lactose. The invention also provides the use of the finely divided particles according to the invention in the manufacture of a medicament for use in the treatment of a respiratory disorder.

The finely divided particles according to the invention may be used in a variety of pharmaceutical formulations, e.g. in producing tablets, or for filling into capsules for oral is use. Preferred, however, are finely divided particles to be used to produce inhalation formulations. Thus the finely divided particles according to the invention may be used on their own or in admixture with excipients, e.g. lactose, which are of a larger, or approximately of the same, particle size as the drug. Such powder formulations may be used in capsules, e.g. for use in the Spinhaler®, or in other inhalation devices, e.g. the Turbuhaler®, the Rotahaler®, the Diskhaler® or Diskus®. The finely divided particles according to the invention may also be treated further using known techniques, e.g. spheronization, to provide soft pellets, or soft granules, which are sufficiently strong to be filled into containers without disintegrating, but which are sufficiently weak to disintegrate into their fine constituent particles when administered by inhalation.

The invention is illustrated by the following Examples which should not be interpreted as limiting the invention.

EXAMPLE 1

An acetone solution containing 1.0% w/v of budesonide was prepared and fed (0.3 ml/min) into the apparatus described in WO 95/01221 using a 0.15 μm nozzle. The flow rate of supercritical carbon dioxide was 10.0 ml/min. The working conditions were 100 bar and 60° C. A fine, smooth, white crystalline powder of budesonide having a BET value of 3.6 $m^2/g$ (measured using a Gemini 2375 V1.01) and a particle size of 2.25 μm (MMD) was obtained in 88% yield. The SEM of the powder is shown in FIG. 1.

EXAMPLE 2

An acetone solution containing 2.5% w/v of budesonide was prepared and fed (0.2 ml/min) into the same apparatus as used in Example 1. The flow rate of supercritical carbon dioxide was 9.0 ml/min. The working conditions were 100 bar and 80° C. A fine, smooth, white crystalline powder of budesonide was obtained which had the X-ray powder diffraction pattern shown in FIG. 2.

EXAMPLE 3

An acetone solution containing 1.0% w/v of budesonide was prepared and fed (1.5 ml/min) into the apparatus described in WO 95/01221 using a 0.35 μm nozzle. The flow rate of supercritical carbon dioxide was 45 ml/min. The working conditions were 100 bar and 60° C. A fine, smooth, white crystalline powder of budesonide having a BET value of 2.0 $m^2/g$ (measured using a Gemini 2375 V1.01) and a particle size of 4.62 μm (MMD) was obtained in 82% yield.

EXAMPLE 4

An acetone solution containing 2.5% w/v of budesonide was prepared and fed (1.5 ml/min) into the apparatus described in WO 95/01221 using a 0.35 μm nozzle. The flow rate of supercritical carbon dioxide was 45 ml/min. The working conditions were 100 bar and 80° C. A fine, smooth, white crystalline powder of budesonide having a BET value of 2.5 $m^2/g$ (measured using a Gemini 2375 V1.01) and a particle size of 3.33 μm (MMD) was obtained in 83% yield.

What is claimed is:

1. A method of manufacturing finely divided particles of budesonide, comprising:
    (a) co-introducing into a vessel (i) a solution of budesonide in a solvent, and (ii) a supercritical fluid; and
    (b) controlling temperature and pressure, during step (a), so that dispersion and extraction of the solvent by the action of the supercritical fluid occur simultaneously; wherein said particles have a BET value from 1 to 4.5 $m^2/g$.
2. A method of claim 1 wherein said particles are crystalline.
3. A method of claim 1 wherein said supercritical fluid comprises carbon dioxide.
4. A method of claim 1 wherein said solvent comprises acetone or methanol.
5. A method according to claim 1, wherein the solvent is an organic solvent.
6. A method according to claim 1, wherein the supercritical fluid is carbon dioxide and in step (b) the temperature is from 60 to 80° C. and the pressure is 100 bar.
7. A method according to claim 1 wherein the solution (i) in step (a) contains from 1.0 to 2.5% w/v of budesonide.
8. A method according to claim 1 wherein the particles are substantially crystalline.
9. A powder comprising finely divided, substantially crystalline particles of budesonide having a BET value of from 1 to 4.5 $m^2/g$, obtained by a process comprising:
    (a) co-introducing into a vessel (i) a solution of budesonide in a solvent, and (ii) a supercritical fluid; and
    (b) controlling temperature and pressure, during step (a), so that dispersion and extraction of the solvent by the action of the supercritical fluid occur simultaneously.
10. A powder according to claim 9 wherein said particles have a BET value of from 2.0 to 3.6 $m^2/g$.
11. A powder according to claim 9 wherein said particles have an energy of recrystallisation of less than 1 J/g.
12. A powder according to claim 9 wherein said particles have a mass median mean diameter of less than 10 μm.
13. A powder according to claim 9 wherein said particles have a mass median mean diameter of less than 5 μm.
14. A powder according to claim 9 wherein said particles have at least 95% by weight crystallinity and are free of amorphous areas.
15. A powder according to claim 9 wherein said particles have 100% by weight crystallinity.

* * * * *